(12) United States Patent
Mair et al.

(10) Patent No.: US 8,664,403 B2
(45) Date of Patent: Mar. 4, 2014

(54) PROCESS

(75) Inventors: Hans-Juergen Mair, Loerrach (DE); Reinhard Reents, Muenchenstein (CH); Michelangelo Scalone, Birsfelden (CH); Shaoning Wang, Basel (CH); Andreas Zogg, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/324,199

(22) Filed: Dec. 13, 2011

(65) Prior Publication Data

US 2012/0157504 A1   Jun. 21, 2012

(30) Foreign Application Priority Data

Dec. 16, 2010 (EP) .................................. 10195294

(51) Int. Cl.
*A61K 31/428* (2006.01)
*C07D 277/64* (2006.01)

(52) U.S. Cl.
USPC ........................... 548/152; 548/146; 514/367

(58) Field of Classification Search
USPC .................................. 548/146, 152; 514/367
See application file for complete search history.

(56) References Cited

U.S. PATENT DOCUMENTS 2,483,447 A    10/1949  Vinton
6,426,365 B1   7/2002   Shinkai et al.

FOREIGN PATENT DOCUMENTS

WO   2007/051714   5/2007
WO   2008/074677   6/2008

OTHER PUBLICATIONS

Shinkai et al., J.Med. Chem., 2000, vol. 43, No. 19.*
Dan, W. et al., Tetrahedron Letters (XP027218172), 66(37):7384-7388 ( 2010).
Chen, R & Zhang, Y., Synthetic Communications (XP009127233), 29(21):3699-3704 ( 1999).
(International Search Report for PCT/EP2011/072470 May 8, 2012).
Lakouraj, M. et al., Monatshefte fur Chemie (XP002635232), 133:1085-1088 ( 2002).
Kesler, P. et al., Tetrahedron Letters 35(39):7237-7240 ( 1994).
Calais, C. et al., Journal of Catalysis (XP002227637), 144:160-174 ( 1993).
Arisawa, M. et al., Tetrahedron Letters (XP002538491), 46(36):6097-6099 ( 2005).
Houben-Weyl, Methoden der Organischen Chemie IV(1c):486-488 ( 1980).
Zymalkowski, Katalytische Hydrierungen im Organisch-Chemischen Laboratorium:34-39 ( 1965).
Kobayashi et al., Atherosclerosis 162:131-135 ( 2002).
De Grooth et al., Circulation 105:2159-2165 ( 2002).
Okamoto et al., Nature 406(13):201-207 ( 2000).
Shinkai et al., J. Med. Chem. 43:3566-3572 ( 2000).

* cited by examiner

*Primary Examiner* — Yong Chu
*Assistant Examiner* — Sonya Wright

(57) ABSTRACT

The present invention relates to a process for the preparation of S-[2-[1-(2-ethylbutyl)cyclohexylcarbonylamino]-phenyl] 2-methylthiopropionate which is useful as a pharmaceutically active compound.

7 Claims, No Drawings

PROCESS

PRIORITY TO RELATED APPLICATION(S)

This application claims the benefit of European Patent Application No. 10195294.3, filed Dec. 16, 2010, which is hereby incorporated by reference in its entirety.

BACKGROUND OF THE INVENTION

S-[2-([[1-(2-ethylbutyl)cyclohexyl]carbonyl]amino)phenyl]2-methylpropanethioate has been shown to be an inhibitor of CETP activity in humans (de Grooth et al., Circulation, 105, 2159-2165 (2002)) and rabbits (Shinkai et al., J. Med. Chem., 43, 3566-3572 (2000); Kobayashi et al., Atherosclerosis, 162, 131-135 (2002); and Okamoto et al., Nature, 406 (13), 203-207 (2000)). S-[2-([[1-(2-ethylbutyl)cyclohexyl] carbonyl]amino)phenyl]2-methylpropanethioate has been shown to increase plasma HDL cholesterol in humans (de Grooth et al., supra) and in rabbits (Shinkai et al., supra; Kobayashi et al., supra; Okamoto et al., supra). Moreover, S-[2-([[1-(2-ethylbutyl)cyclohexyl]carbonyl]amino)phenyl] 2-methylpropanethioate has been shown to decrease LDL cholesterol in humans (de Grooth et al., supra) and rabbits (Okamoto et al., supra). Additionally, S-[2-([[1-(2-ethylbutyl)cyclohexyl]carbonyl]amino)phenyl]2-methylpropanethioate inhibits the progression of atherosclerosis in rabbits (Okamoto et al., supra).

SUMMARY OF THE INVENTION

The present invention relates to a process for the preparation of S-[2-[1-(2-ethylbutyl)cyclohexylcarbonylamino]-phenyl]2-methylthiopropionate which is useful as a pharmaceutically active compound.

DETAILED DESCRIPTION OF THE INVENTION

Unless otherwise stated, the following terms used in the specification and claims have the meanings given below:

The term "halo" or "halide" means fluoro, chloro, bromo or iodo. In particular embodiments, the halo is chloro or bromo.

The term "$(C_1-C_8)$alkyl" refers to a branched or straight hydrocarbon chain of one to eight carbon atoms. Examples include, but are not limited to, methyl, ethyl, n-propyl, isopropyl, n-butyl, isobutyl, sec-butyl, t-butyl, ethyl-butyl, pentyl, hexyl, heptyl and octyl.

The term "$(C_1-C_8)$alkoxy" means a moiety of the formula —$OR^{ab}$, wherein $R^{ab}$ is a $(C_1-C_8)$alkyl moiety as defined herein. Examples of alkoxy moieties include, but are not limited to, methoxy, ethoxy, isopropoxy, and the like.

The term "$(C_3-C_8)$cycloalkyl" refers to a single saturated carbocyclic ring of three to eight ring carbons. Examples include cyclopropyl, cyclobutyl, cyclopentyl and cyclohexyl. The $(C_3-C_8)$cycloalkyl may optionally be substituted with one or more substituents, preferably one, two or three, substituents. Preferably, the $(C_3-C_8)$cycloalkyl substituent is selected from the group consisting of a $(C_1-C_8)$alkyl, hydroxy, $(C_1-C_8)$alkoxy, halo$(C_1-C_8)$alkyl, halo$(C_1-C_8)$ alkoxy, halo, amino, mono- and di-$(C_1-C_8)$alkylamino, hetero$(C_1-C_8)$alkyl, acyl, aryl and heteroaryl.

The term "aryl" means a monovalent monocyclic or bicyclic aromatic hydrocarbon moiety which is optionally substituted with one or more substituents. Preferably, the aryl is substituted with one, two or three substituents, each of which is preferably selected from the group consisting of a $(C_1-C_8)$ alkyl, hydroxy, $(C_1-C_8)$alkoxy, amino, mono- and di-$(C_1-C_8)$ alkylamino, carboxy, $(C_1-C_8)$alkylsulfonyl, —$SO_2$-aryl, —$SO_3H$, —$SO_3$—$(C_1-C_8)$alkyl or —$SO_2$—$NR^{ac}_2$, wherein each $R^{ac}$ is independently hydrogen or a $(C_1-C_8)$alkyl. More specifically the term aryl includes, but is not limited to, phenyl, 1-naphthyl, 2-naphthyl, and the like, each of which can be substituted or unsubstituted.

The term "heteroaryl" means a monovalent monocyclic or bicyclic moiety of 5 to 12 ring atoms having at least one aromatic ring containing one, two, or three ring heteroatoms selected from N, O, or S with the remaining ring atoms being carbon, with the understanding that the attachment point of the heteroaryl moiety will be on an aromatic ring. Preferably, the ring heteroatoms are N or O. The heteroaryl ring can be optionally substituted independently with one or more substituents, preferably one, two or three substituents, each of which is independently selected from a $(C_1-C_8)$alkyl, halo $(C_1-C_8)$alkyl, hydroxy, $(C_1-C_8)$alkoxy, halo, nitro and cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

The term "heterogeneous transition metal hydrogenation catalyst" refers to a transition metal hydrogenation catalyst which acts in a different phase than the substrate. Preferably, the heterogeneous transition metal hydrogenation catalyst is in the solid phase. In particular, while the heterogeneous transition metal hydrogenation catalyst is in the solid phase the reactants are in the liquid phase. The heterogeneous transition metal hydrogenation catalyst contains a transition metal which forms one or more stable ions which have incompletely filled d orbitals (i.e. Pd, Pt, Rh, Au, Ni, Co, Ru, Ir) in a particular noble metal, such as Pd, Pt, Rh or Au. In these catalysts the transition metal is in particular "supported", which means that the catalyst is dispersed on a second material that enhances the effectiveness. The "support" can be merely a surface on which the metal is spread to increase the surface area. The supports are porous materials with a high surface area, most commonly alumina or various kinds of carbon. Further examples of supports include, but are not limited to, silicon dioxide, titanium dioxide, calcium carbonate, barium sulfate, diatomaceous earth and clay. The metal itself can also act as a support, if no other support is present. More specifically, the term "heterogeneous transition metal hydrogenation catalyst" includes but is not limited to, a Raney catalyst (e.g. Ra—Ni, Ra—Co) Pd/C, Pd(OH)$_2$/C, Au/TiO$_2$, Rh/C, Ru/Al$_2$O$_3$, Ir/CaCO$_3$, or Pt/C. In a particular embodiment, the "heterogeneous transition metal hydrogenation catalyst" is not pre-treated with sulphide.

The term "area %" for a substance A refers to the (area of substance A)/(sum of areas of all peaks)×100, area as obtained from HPLC or GC analysis.

In particular embodiments, the chemical groups whose definitions are given above are those specifically exemplified in the examples.

Unless otherwise stated, all percentages are given in weight percent of the total weight of the compound of formula (I).

In a first embodiment, the invention provides a process for the preparation of a compound of formula (I"):

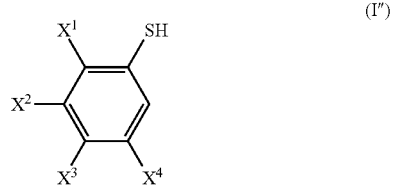

(I″)

wherein $X^1$, $X^2$, $X^3$ and $X^4$ are each independently hydrogen, $(C_1-C_8)$alkyl, aryl, heteroaryl, —$OR^a$, —O—C(=O)$R^b$, —$NHR^c$, —NH—C(=O)$R^d$ or —$NR^e_2$; or two adjacent substituents (i.e. $X^1$ and $X^2$ or $X^2$ and $X^3$ or $X^3$ and $X^4$) together with the carbon atoms to which they are attached form a four, five or six membered cycloalkyl ring that optionally includes an additional heteroatom selected from the group consisting of O, NH, and S wherein the four, five or six membered cycloalkyl ring is optionally substituted with one to three substituents independently selected from the group consisting of a $(C_1-C_8)$alkyl and aryl;

$R^a$, $R^b$, $R^c$ and $R^d$ are independently a $(C_1-C_8)$alkyl, a $(C_3-C_8)$cycloalkyl, aryl or heteroaryl;

each $R^e$ is independently hydrogen, a $(C_1-C_8)$alkyl or aryl; which comprises reacting a compound of formula (II″):

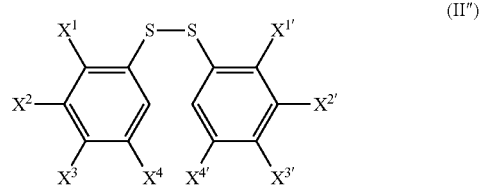

(II″)

wherein $X^{1'}$, $X^{2'}$, $X^{3'}$ and $X^{4'}$ are each independently hydrogen, a $(C_1-C_8)$alkyl, aryl, heteroaryl, —$OR^a$, —O—C(=O)$R^b$, —$NHR^c$, —NH—C(=O)$R^d$ or —$NR^e_2$; or two adjacent substituents (i.e. $X^{1'}$ and $X^{2'}$ or $X^{2'}$ and $X^{3'}$ or $X^{3'}$ and $X^{4'}$) together with the carbon atoms to which they are attached form a four, five or six membered cycloalkyl ring that optionally includes an additional heteroatom selected from the group consisting of O, NH, and S wherein the four, five or six membered cycloalkyl ring is optionally substituted with one to three substituents independently selected from the group consisting of a $(C_1-C_8)$alkyl and aryl; and $R^a$, $R^b$, $R^c$, $R^d$, $R^e$, $X^1$, $X^2$, $X^3$ and $X^4$ are as defined above, with $H_2$ in the presence of a heterogeneous transition metal hydrogenation catalyst.

Common reduction disulfide processes result inter alia to similar disadvantages. They use reducing agents in stoichiometric amounts leading to safety issues, large amounts of waste and/or laborious work-up. Although these disadvantages on lab scale may not be seen of great importance, when going on large production scale they are looked at carefully due their factorial impact.

The S—S disulfide bonds (and the S—H bonds formed during the hydrogenation) are considered as catalyst poisons, due to the strong chemisorptions of sulfur-containing molecules on metal surfaces (Houben-Weyl, Methoden der Organischen Chemie, Band IV/1c, published 1980, page 486; or F. Zymalkowski, Katalytische Hydrierungen im Organisch-Chemischen Laboratorium, F. Enke Verlag Stuttgart, published 1965, page 37). Therefore, it was surprisingly found that the reduction of a disulfide bond according to the present invention is selective with high throughput.

The present invention does not require a pretreatment of the catalyst, in particular, there is no need of sulfide pretreatment of the catalysts.

In a second embodiment, the invention provides a process for the preparation of a compound of formula (I‴):

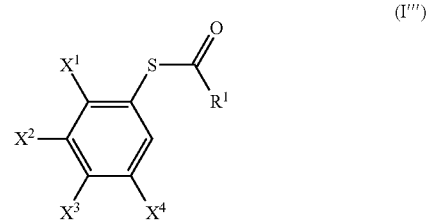

(I‴)

wherein $X^1$, $X^2$, $X^3$ and $X^4$ are each independently hydrogen, a $(C_1-C_8)$alkyl, aryl, heteroaryl, —$OR^a$, —O—C(=O)$R^b$, —$NHR^c$, —NH—C(=O)$R^d$ or —$NR^e_2$; or two adjacent substituents (i.e. $X^1$ and $X^2$ or $X^2$ and $X^3$ or $X^3$ and $X^4$) together with the carbon atoms to which they are attached form a four, five or six membered cycloalkyl ring that optionally includes an additional heteroatom selected from the group consisting of O, NH, and S wherein the four, five or six membered cycloalkyl ring is optionally substituted with one to three substituents independently selected from the group consisting of a $(C_1-C_8)$alkyl and aryl;

$R^1$ is a $(C_1-C_8)$alkyl or aryl;

$R^a$, $R^b$, $R^c$ and $R^d$ are independently a $(C_1-C_8)$alkyl, $(C_3-C_8)$cycloalkyl, aryl or heteroaryl;

each $R^e$ is independently hydrogen, $(C_1-C_8)$alkyl or aryl; which comprises reacting a compound of formula (II″):

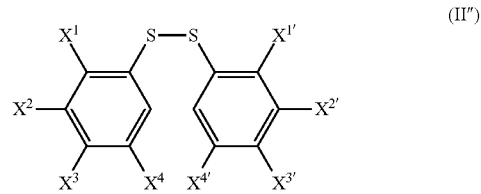

(II″)

wherein $X^{1'}$, $X^{2'}$, $X^{3'}$ and $X^{4'}$ are each independently hydrogen, $(C_1-C_8)$alkyl, aryl, heteroaryl, —$OR^a$, —O—C(=O)$R^b$, —$NHR^c$, —NH—C(=O)$R^d$ or —$NR^e_2$; or two adjacent substituents (i.e. $X^{1'}$ and $X^{2'}$ or $X^{2'}$ and $X^{3'}$ or $X^{3'}$ and $X^{4'}$) together with the carbon atoms to which they are attached form a four, five or six membered cycloalkyl ring that optionally includes an additional heteroatom selected from the group consisting of O, NH and S, wherein the four, five or six membered cycloalkyl ring is optionally substituted with one to three substituents independently selected from the group consisting of a $(C_1-C_8)$alkyl and aryl; and $R^a$, $R^b$, $R^c$, $R^d$, $R^e$, $X^1$, $X^2$, $X^3$ and $X^4$ are as defined above, with $H_2$ in the presence of an acylating agent such as an anhydride derivative [(($C_1-C_8$)alkyl)C(=O)]$_2$O or [aryl(C=O)]$_2$O or a halide derivative (($C_1-C_8$)alkyl)C(=O)halide or aryl(C=O)halide and a heterogeneous transition metal hydrogenation catalyst.

In another embodiment, the present invention provides a process for the preparation of a compound of formula (I″):

(I'')

[Structure: benzene ring with X¹, SH, X², X³, X⁴ substituents]

wherein

X¹ is —NH—C(=O)R$^d$, wherein R$^d$ is a (C$_3$-C$_8$)cycloalkyl substituted by a (C$_1$-C$_8$)alkyl, in particular R$^d$ is (2-Ethyl-butyl)-cyclohexyl;

X², X³ and X⁴ are each independently hydrogen, a (C$_1$-C$_8$) alkyl, aryl, heteroaryl, —OR$^a$, —O—C(=O)R$^b$, —NHR$^c$, —NH—C(=O)R$^d$ or —NR$^e{}_2$, in particular X², X³ and X⁴ are each independently hydrogen or a (C$_1$-C$_8$)alkyl;

R$^a$, R$^b$, R$^c$ and R$^d$ are independently a (C$_1$-C$_8$)alkyl, a (C$_3$-C$_8$)cycloalkyl, aryl or heteroaryl;

each R$^e$ is independently hydrogen, a (C$_1$-C$_8$)alkyl or aryl;

which comprises reacting a compound of formula (II''):

(II'')

[Structure: two benzene rings connected by S—S disulfide bridge with substituents X¹, X², X³, X⁴ on one ring and X¹', X²', X³', X⁴' on the other]

wherein X¹' is —NH—C(=O)R$^d$ or —NR$^e{}_2$;

R$^d$ is a (C$_3$-C$_8$)cycloalkyl substituted by a (C$_1$-C$_8$)alkyl, in particular embodiments R$^d$ is (2-Ethyl-butyl)-cyclohexyl;

R$^{e'}$ is hydrogen;

X²', X³' and X⁴' are each independently hydrogen, a (C$_1$-C$_8$) alkyl, aryl, heteroaryl, —OR$^a$, —O—C(=O)R$^b$, —NHR$^c$, —NH—C(=O)R$^d$ or —NR$^e{}_2$, in particular embodiments X², X³ and X⁴ are each independently hydrogen or a (C$_1$-C$_8$)alkyl; and R$^a$, R$^b$, R$^c$, R$^d$, R$^e$, X¹, X², X³ and X⁴ are as defined above, with H$_2$ in the presence of a heterogeneous transition metal hydrogenation catalyst.

In another embodiment, the present invention provides a process for the preparation of a compound of formula (I'''):

(I''')

[Structure: benzene ring with X¹, S—C(=O)R¹, X², X³, X⁴ substituents]

wherein

X¹ is —NH—C(=O)R$^d$, wherein R$^d$ is a (C$_3$-C$_8$)cycloalkyl substituted by a (C$_1$-C$_8$)alkyl, in particular embodiments R$^d$ is (2-Ethyl-butyl)-cyclohexyl;

X², X³ and X⁴ are each independently hydrogen, a (C$_1$-C$_8$) alkyl, aryl, heteroaryl, —OR$^a$, —O—C(=O)R$^b$, —NHR$^c$, —NH—C(=O)R$^d$ or —NR$^e{}_2$, in particular embodiments X², X³ and X⁴ are each independently hydrogen or (C$_1$-C$_8$)alkyl;

R$^a$, R$^b$, R$^c$ and R$^d$ are independently a (C$_1$-C$_8$)alkyl, a (C$_3$-C$_8$)cycloalkyl, aryl or heteroaryl;

each R$^e$ is independently hydrogen, a (C$_1$-C$_8$)alkyl or aryl;

R¹ is a (C$_1$-C$_8$)alkyl or aryl;

which comprises reacting a compound of formula (II''):

(II'')

[Structure: two benzene rings connected by S—S disulfide bridge with substituents X¹, X², X³, X⁴ and X¹', X²', X³', X⁴']

wherein X¹' is —NH—C(=O)R$^d$ or —NR$^{e'}{}_2$;

R$^d$ is a (C$_3$-C$_8$)cycloalkyl substituted by a (C$_1$-C$_8$)alkyl, in particular embodiments R$^d$ is (2-ethyl-butyl)-cyclohexyl;

R$^{e'}$ is hydrogen;

X²', X³' and X⁴' are each independently hydrogen, a (C$_1$-C$_8$) alkyl, aryl, heteroaryl, —OR$^a$, —O—C(=O)R$^b$, —NHR$^c$, —NH—C(=O)R$^d$ or —NR$^e{}_2$, in particular embodiments X², X³ and X⁴ are each independently hydrogen or (C$_1$-C$_8$)alkyl; and R$^a$, R$^b$, R$^c$, R$^d$, R$^e$, X¹, X², X³ and X⁴ are as defined above, with H$_2$ in the presence of a heterogeneous transition metal hydrogenation catalyst.

In a further embodiment the present invention provides a process for the preparation of compound of formula (I'):

(I')

[Structure: compound with cyclohexyl group attached to C(=O)NH-phenyl-SH with 2-ethylbutyl substituent]

which comprises reacting a compound of formula (II'):

(II')

[Structure: dimer with S—S disulfide bridge, two phenyl-NH-C(=O)-cyclohexyl-(2-ethylbutyl) groups]

wherein R is H or with a compound of the formula

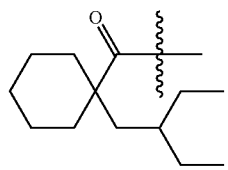

with $H_2$ in the presence of a heterogeneous transition metal hydrogenation catalyst.

In a further embodiment the present invention provides a process for the preparation of the compounds of formula (I') and Formula (X):

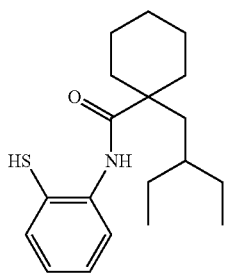

(I')

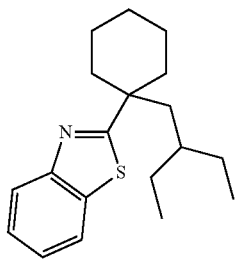

(X)

which comprises reacting a compound of formula (II'):

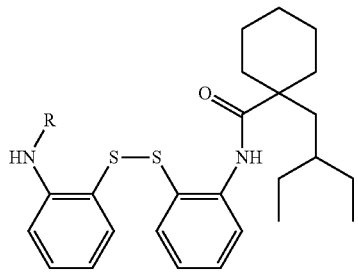

(II')

wherein R is H or with a compound of the formula

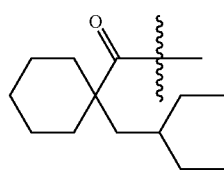

with $H_2$ in the presence of a heterogeneous transition metal hydrogenation catalyst.

In another embodiment, the present invention provides a process for the preparation of compounds of formula (I') and Formula (X):

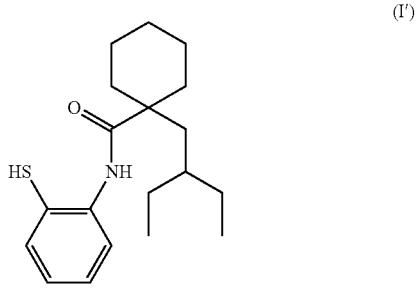 [SMILES: CCC(CC)CC1(C(=O)Nc2ccccc2S)CCCCC1]

(I')

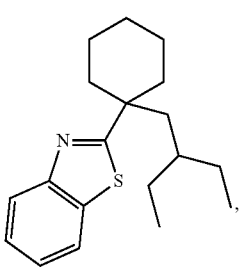

(X)

which comprises reacting a compound of formula (II):

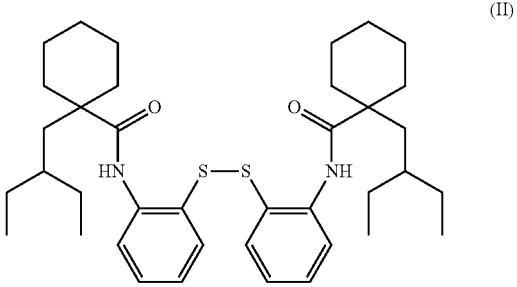 [SMILES: CCC(CC)CC1(C(=O)Nc2ccccc2SSc2ccccc2NC(=O)C2(CC(CC)CC)CCCCC2)CCCCC1]

(II)

with $H_2$ in the presence of a heterogeneous transition metal hydrogenation catalyst.

In another embodiment the present invention provides a process for the preparation of a compound of formula (I'):

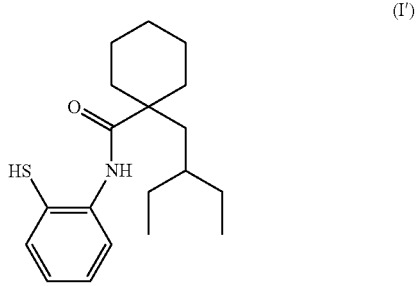 [SMILES: CCC(CC)CC1(C(=O)Nc2ccccc2S)CCCCC1]

(I')

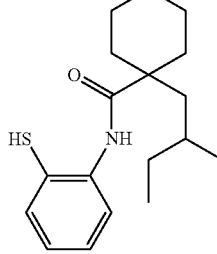

which comprises reacting a compound of formula (II):

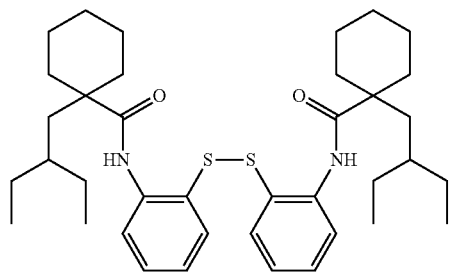

(II)

with $H_2$ in the presence of a heterogeneous transition metal hydrogenation catalyst.

In another embodiment, the present invention provides a process for the preparation of a compound of formula (Ia):

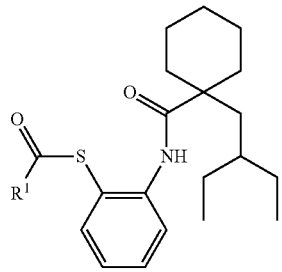

(Ia)

wherein $R^1$ is a $(C_1-C_8)$alkyl or aryl, in particular $R^1$ is isopropyl, which comprises reacting a compound of formula (II'):

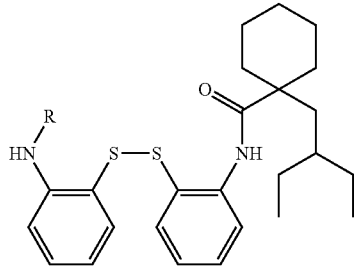

(II')

wherein R is H or a compound of the formula:

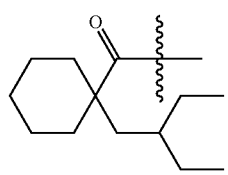

with $H_2$ in the presence of an acylating agent such as an anhydride derivative $[((C_1-C_8)alkyl)C(=O)]_2O$ or $[aryl(C=O)]_2O$ or a halide derivative $((C_1-C_8)alkyl)C(=O)$halide or aryl(C=O)halide and a heterogeneous transition metal hydrogenation catalyst. In particular, when $R^1$ is isopropyl, the acylating agent is isobutyric anhydride or isobutyryl halide, in particular isobutyric anhydride.

In another embodiment, the present invention provides a process for the preparation of compounds of formula (Ia) and Formula (X):

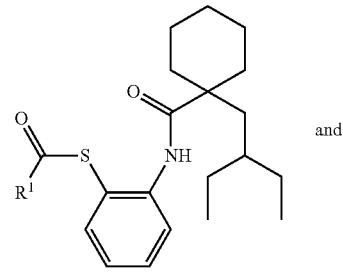

(Ia)

and

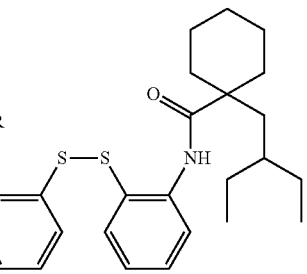

(X)

wherein $R^1$ is a $(C_1-C_8)$alkyl or aryl, and in particular embodiments $R^1$ is isopropyl, which comprises reacting a compound of formula (II'):

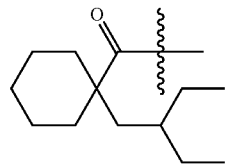 [SMILES: *C(=O)C1(CC(CC)CC)CCCCC1]

(II')

wherein R is H or a compound of the formula:

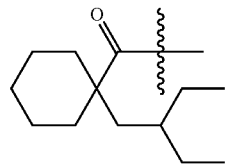 [SMILES: *C(=O)C1(CC(CC)CC)CCCCC1]

with $H_2$ in the presence of an acylating agent such as an anhydride derivative $[((C_1-C_8)alkyl)C(=O)]_2O$ or $[aryl(C=O)]_2O$ or a halide derivative $((C_1-C_8)alkyl)C(=O)$halide or aryl(C=O)halide and a heterogeneous transition metal hydrogenation catalyst. In particular, when $R^1$ is isopropyl, the acylating agent is isobutyric anhydride or isobutyryl halide, in particular isobutyric anhydride.

In another embodiment, the present invention provides a process for the preparation of a compound of formula (I):

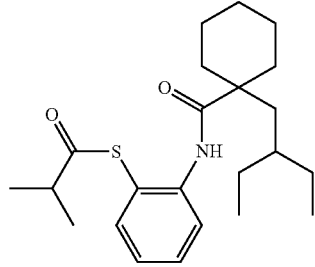
(I)

which comprises reacting a compound of formula (II'):

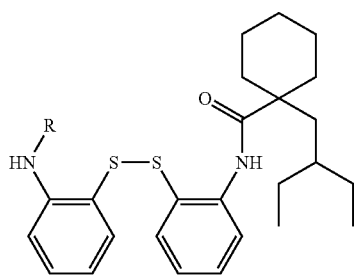
(II')

wherein R is H or a compound of the formula:

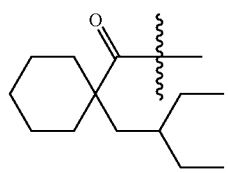

with $H_2$ in the presence of acylating agent such as isobutyric anhydride or isobutyryl halide, and more particularly the acylating agent is isobutyric anhydride.

In another embodiment, the present invention provides a process for the preparation of compounds of formula (I) and Formula (X):

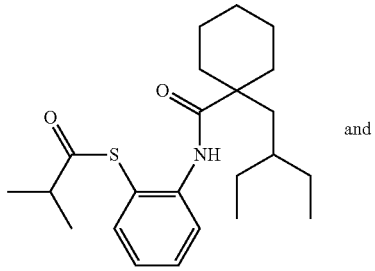
(I)

and

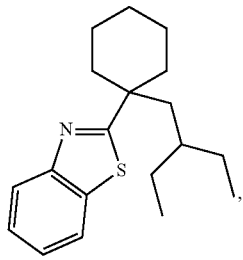
(X)

which comprises reacting a compound of formula (II'):

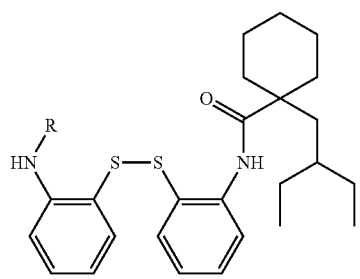
(II')

wherein R is H or a compound of the formula:

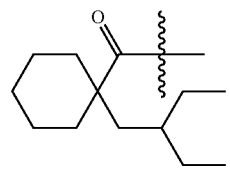 [SMILES: *C(=O)C1(CC(CC)CC)CCCCC1]

with $H_2$ in the presence of acylating agent such as isobutyric anhydride or isobutyryl halide, and more particularly the acylating agent is isobutyric anhydride.

In another embodiment, the present invention provides a process for the preparation of a compound of formula (Ia):

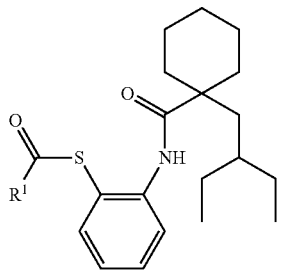
(Ia)

wherein $R^1$ is a $(C_1-C_8)$alkyl or aryl, and in particular embodiments $R^1$ is isopropyl, which comprises reacting a compound of formula (II):

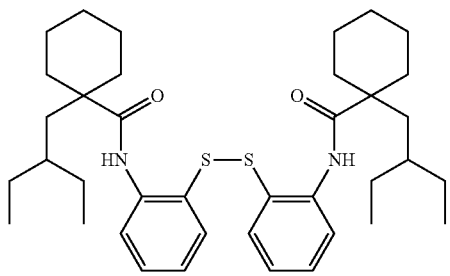
(II)

with H$_2$ in the presence of an acylating agent such as an anhydride derivative [((C$_1$-C$_8$)alkyl)C(=O)]$_2$O or [aryl(C=O)]$_2$O or a halide derivative ((C$_1$-C$_8$)alkyl)C(=O)halide or aryl(C=O)halide and a heterogeneous transition metal hydrogenation catalyst. In particular, when R$^1$ is isopropyl, the acylating agent is isobutyric anhydride or isobutyryl halide, and in particular isobutyric anhydride.

In another embodiment, the present invention provides a process for the preparation of the compounds of formula (Ia) and Formula (X):

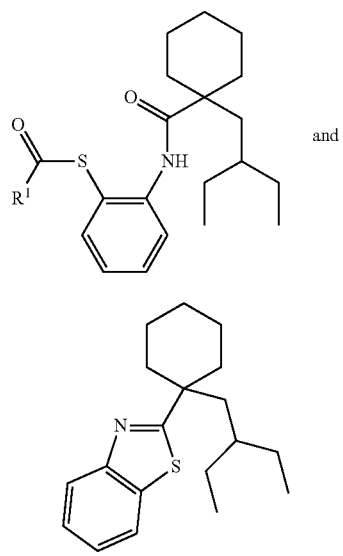

wherein R$^1$ is a (C$_1$-C$_8$)alkyl or aryl, and in particular embodiments R$^1$ is isopropyl, which comprises reacting a compound of formula (II):

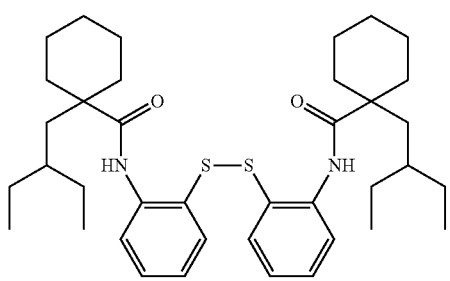
(II)

with H$_2$ in the presence of an acylating agent such as an anhydride derivative [((C$_1$-C$_8$)alkyl)C(=O)]$_2$O or [aryl(C=O)]$_2$O or a halide derivative ((C$_1$-C$_8$)alkyl)C(=O)halide or aryl(C=O)halide and a heterogeneous transition metal hydrogenation catalyst. In particular embodiments, when R$^1$ is isopropyl, the acylating agent is isobutyric anhydride or isobutyryl halide, and in particular embodiments isobutyric anhydride.

In another embodiment, the present invention provides a process for the preparation of a compound of formula (I):

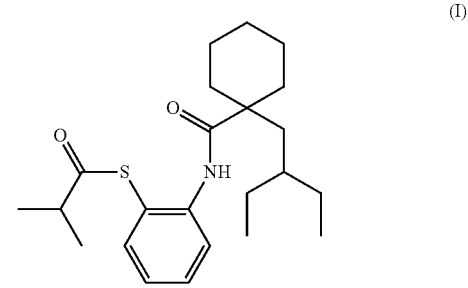 [SMILES: CCC(CC)CC1(C(=O)Nc2ccccc2SC(=O)C(C)C)CCCCC1]
(I)

which comprises reacting a compound of formula (II):

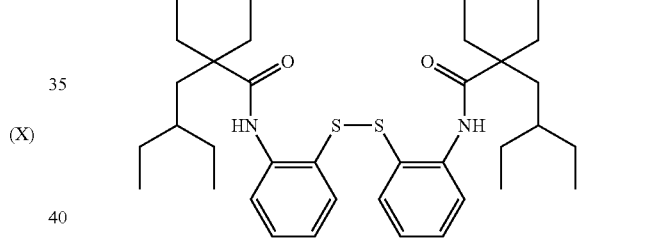
(II)

with H$_2$ in the presence of an acylating agent such as isobutyric anhydride or isobutyryl halide, and in particular embodiments isobutyric anhydride.

In another embodiment, the present invention provides a process for the preparation of compounds of formula (I) and Formula (X):

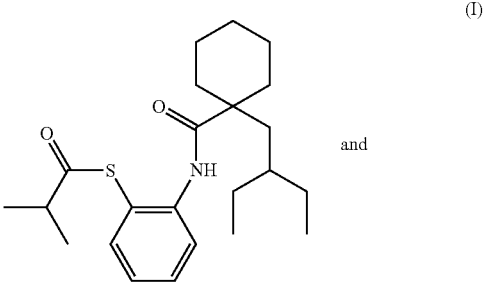
(I)

-continued

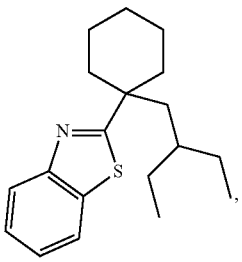
(X)

which comprises reacting a compound of formula (II):

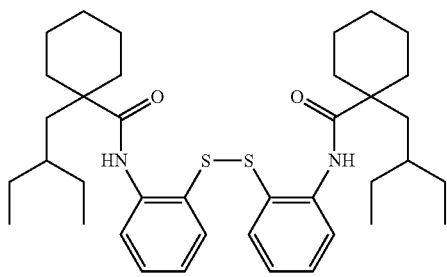
(II)

with $H_2$ in the presence of acylating agent such as isobutyric anhydride or isobutyryl halide, and
in particular embodiments isobutyric anhydride.

In particular embodiments, the present invention provides a process for the preparation of S-[2-([[1-(2-ethylbutyl)-cyclohexyl]-carbonyl]amino)phenyl]2-methylpropanethioate comprising the formation of a compound of formula (I'):

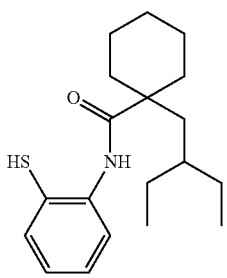
(I')

which comprises reacting a compound of formula (II):

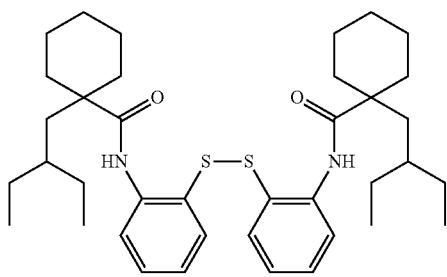
(II)

with $H_2$ in the presence of a heterogeneous transition metal hydrogenation catalyst.

The present invention as described above may be carried out in the presence of a solvent or a mixture of two or more solvents. In particular the solvent is an organic solvent such as an ether like solvent (e.g. tetrahydrofuran, methyltetrahydrofuran, diisopropyl ether, t-butylmethyl ether or dibutyl ether), ester like solvent (e.g. ethyl acetate, isopropyl acetate butyl acetate), aliphatic hydrocarbon solvent (e.g. hexane, heptane or pentane), saturated alicyclic hydrocarbon solvent (e.g. cyclohexane or cyclopentane), or aromatic solvent (e.g. toluene, o- m- or p-xylene or t-butyl-benzene), or a mixture thereof. In particular, the hydrogenation step according to the present invention is carried out in the presence of a solvent selected from an ether like solvent, ester like solvent, aliphatic hydrocarbon solvent, saturated alicyclic hydrocarbon solvent, aromatic solvent, and mixtures thereof, when no acylating agent is present; and in particular embodiments the solvent is an aliphatic hydrocarbon solvent, saturated alicyclic hydrocarbon solvent or aromatic solvent.

In another embodiment the anhydride derivative can act as a solvent or co-solvent, e.g. molar ratio anhydride/amidodisulfide of 2 to 20, and in particular 2 to 5.

In a particular embodiment, the present invention provides a process as described above, wherein the acylating agent is isobutyric anhydride. In particular embodiments, 2.0 to 4.0 equivalents of isobutyric anhydride with respect to the disulfide of formula (II) are used. More particularly, 2.5 to 3.5 equivalents are used.

In a particular embodiment, the present invention provides a process as described above wherein the reaction is carried out at temperature up to 150° C., in particular between 25° C. and 150° C., more particularly between 60° C. to 90° C., most particularly at 80° C.

In a particular embodiment, the present invention provides a process as described above wherein the $H_2$ is added at a pressure of at least 0.1 bar, particularly at a pressure between 0.1 to 100 bar, more particularly at a pressure between 0.2 bar to 30 bar, most particularly 5 to 25 bar.

In a particular embodiment, the present invention provides a process as described above wherein the heterogeneous transition metal hydrogenation catalyst is a Raney catalyst, Pd/C, Pd(OH)$_2$/C, Nanoparticulate Palladium(0) microencapsulated in polyurea matrix (NP Pd(0) Encat™ 30), Au/TiO$_2$, Rh/C, Ru/Al$_2$O$_3$, Ir/CaCO$_3$, or Pt/C, or a mixture thereof, particularly the heterogeneous transition metal hydrogenation catalyst is a Raney catalyst, Pd/C, Pd(OH)$_2$/C, Au/TiO$_2$, Rh/C, Ru/Al$_2$O$_3$, Ir/CaCO$_3$, or Pt/C, or a mixture thereof, more particularly the heterogeneous transition metal hydrogenation catalyst is Pd/C, Pd(OH)$_2$/C, Au/TiO$_2$, Rh/C, Ra—Ni or Pt/C, and most particularly the heterogeneous transition metal hydrogenation catalyst is Pd/C or Ra—Ni. The hydrogenation can be run in the presence of a molar excess of palladium towards the disulfide. More conveniently, palladium is used in catalytic amounts, e.g. 0.001 to 0.1 equivalents, preferably 0.01 to 0.1 equivalents with respect to the disulfide. The catalyst can be re-used several times such that the ratio between the disulfide converted and the moles of palladium employed is increased correspondingly.

In another embodiment, the present invention provides a compound of formula (X):

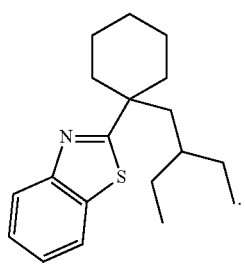
(X)

In another embodiment the present invention provides a composition comprising a compound of formula (I):

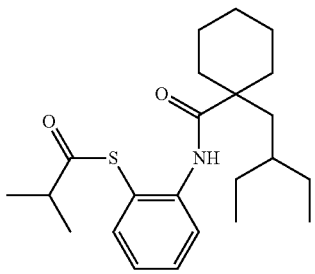
(I)

and comprising a compound of formula (X):

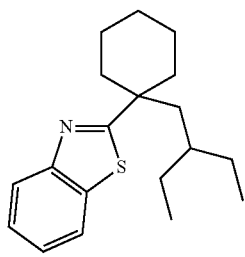
(X)

and having less than 0.1% of the compound of formula (X) by weight.

In another embodiment, the present invention provides a composition comprising a compound of formula (I):

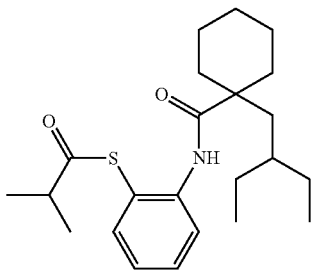
(I)

and comprising a compound of formula (X):

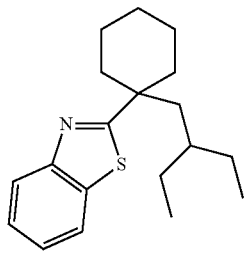
(X)

and having between 1 ppb (parts per billion in weight) and 100 ppm (parts per million in weight) of the compound of formula (X), and in particular embodiments having between 1 ppb and 1 ppm of the compound of formula (X).

Compounds of formulae (I') and (X) can be prepared according to scheme 1 wherein the process conditions are herein described:

Scheme 1:

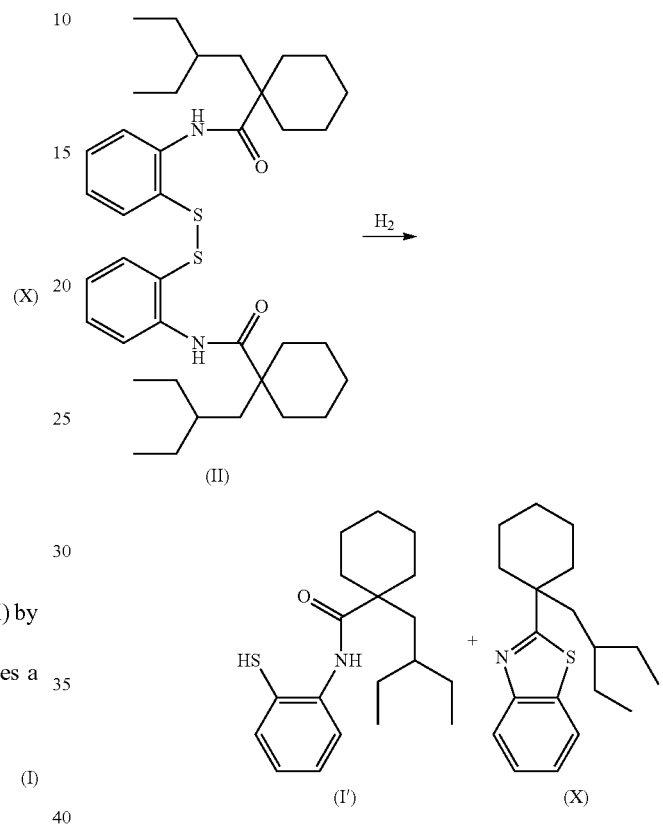

Compounds of formulae (I) and (X) can be prepared according to scheme 2 wherein the process conditions are herein described:

Scheme 2:

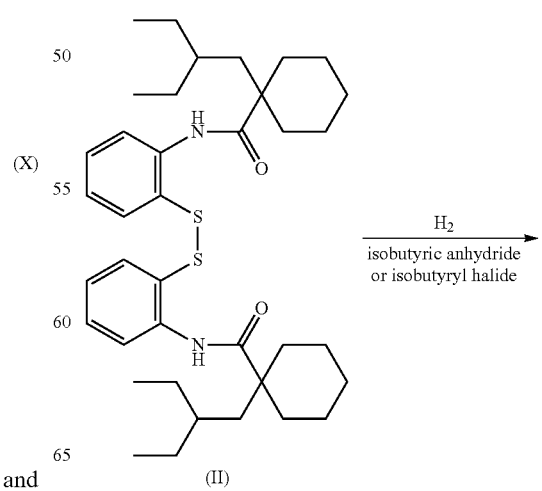

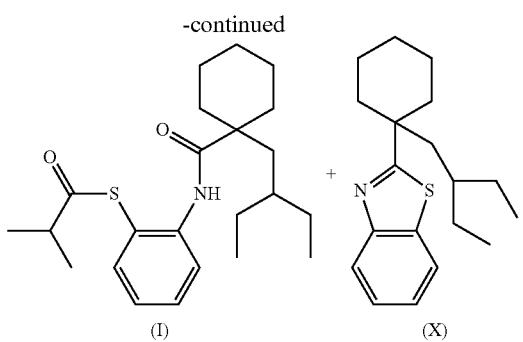

Compounds of formulae (II) and (II') can be prepared according to scheme 3:

Scheme 3:

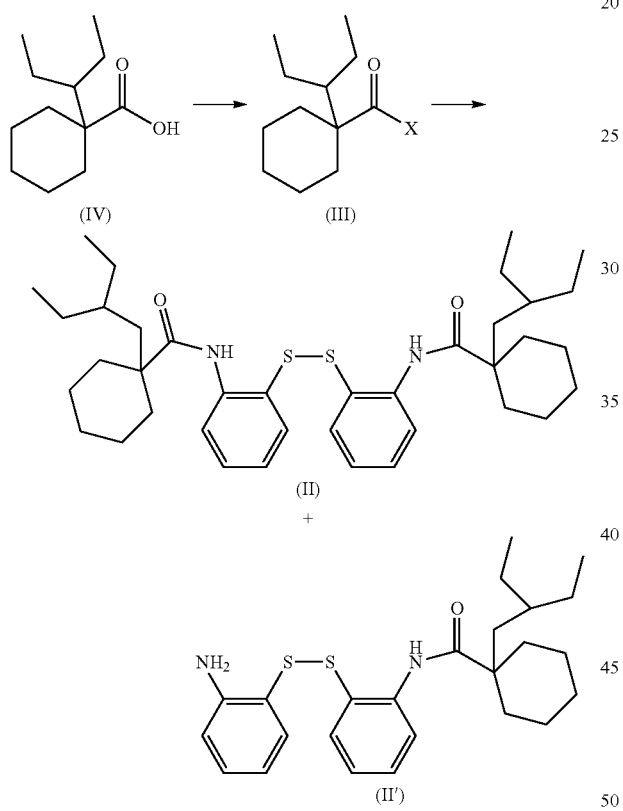

wherein X is I, Br, Cl or F. In particular, the process comprises reacting a cyclohexanecarboxylic acid derivative of formula (IV) with a halogenating agent, such as $PX_3$, $PX_5$, $SOX_2$ or NCX, $COX_2$ to obtain the acyl halide of formula (III). The halogenating step is preferably carried out in the presence of tri-($C_1$-$C_5$)alkylamine. Furthermore, the process comprises reacting an acyl halide with bis(2-aminophenyl)disulfide to acylate the amino groups of the bis(2-aminophenyl)disulfide in the presence of a base (e.g. N-methylmorpholine, di-N-methylpiperazine, or pyridine).

The starting materials, reagents and catalysts, which do not have their synthetic route explicitly disclosed herein, are generally available from commercial sources or are readily prepared using methods known to the person skilled in the art. For instance, the compounds of formulae (II) and (IV) can be prepared according to the procedures described in Shinkai et al., J. Med. Chem. 43:3566-3572 (2000), WO 2007/051714, or WO 2008/074677.

The preparation of the compound of formula (IV) comprises the preparation of a cyclohexanecarbonitrile derivative of formula (VI) followed by the hydrolysis steps as described hereunder and in the following scheme 4.

Scheme 4:

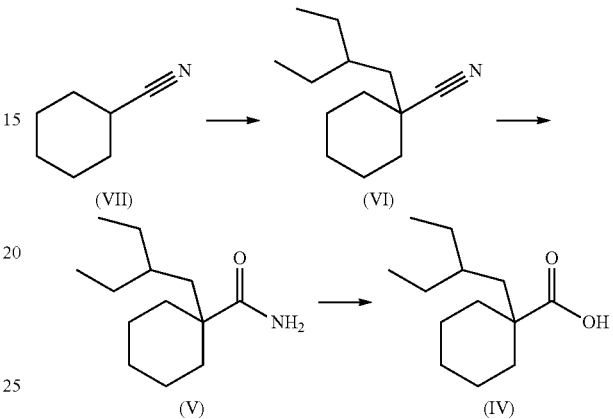

The compound of formula (VI) can be prepared by reacting compound of formula (VII):

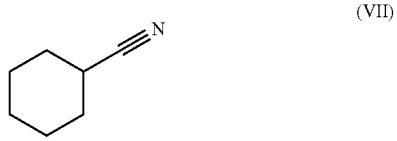

with an alkylating agent such as 1-halo-2-ethylbutane, or 2-ethyl-1-butanol and a Grignard reagent, such as a ($C_1$-$C_6$) alkyl-magnesium-halide, phenyl-magnesium-halide, heteroaryl-magnesium-halide or a ($C_3$-$C_6$)cycloakyl-magnesium-halide. In particular, the above mentioned coupling reaction is carried out in the presence of a secondary amine. In particular, the Grignard reagent is added to the cyclohexanecarbonitrile, and more particularly in the presence of a secondary amine, followed by the addition of an alkylating agent, as defined above. In particular, the above mentioned coupling reaction is followed by a mineral acid quenching, such as hydrofluoric acid, hydrochloric acid, boric acid, acetic acid, formic acid, nitric acid, phosphoric acid or sulfuric acid, most particularly by hydrochloric acid.

The compound of formula (IV) can be prepared by the following steps:
a) hydrolysis of a cyclohexanecarbonitrile derivative of formula (VI):

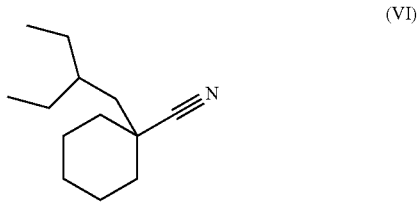

with H₂O in the presence of a strong acid, or with an aqueous base, to obtain a cyclohexanecarboxylic acid amide derivative of formula (V):

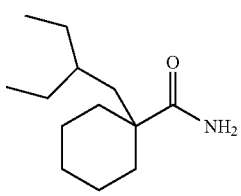
(V)

b) react the cyclohexanecarboxylic acid amide derivative of formula (V) with a nitrosylating agent, to obtain the compound of formula (IV). The nitrosylating agent can be generated in situ e.g. mixing H₂SO₄ and nitrous acid (HNO₂) or H₂SO₃/HNO₃ or N₂O₃/H₂SO₄ or HNO₃/SO₂ to obtain nitrosulfuric acid (NOHSO₄).

In another embodiment, the present invention provides a composition comprising a compound of formula (I):

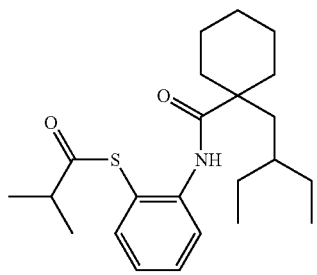
(I)

and comprising a compound of formula (V):

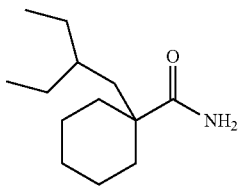
(V)

and having less than 0.1% of the compound of formula (V) by weight.

In another embodiment, the present invention provides a composition comprising a compound of formula (I):

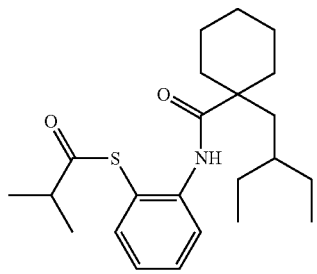
(I)

comprising a compound of formula (V):

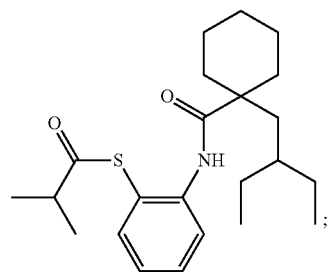
(V)

and having between 1 ppb (parts per billion in weight) and 100 ppm (parts per million in weight) of the compound of formula (V), and in particular embodiments having between 1 ppb and 1 ppm of the compound of formula (V).

In another embodiment, the present invention provides a composition comprising:
a compound of formula (I):

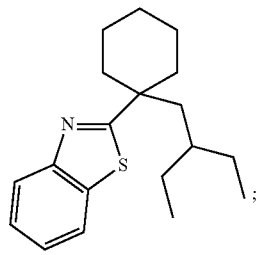
(I)

a compound of formula (X):

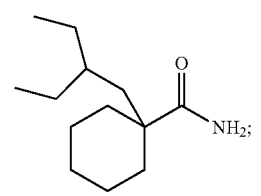
(X)

and a compound of formula (V)

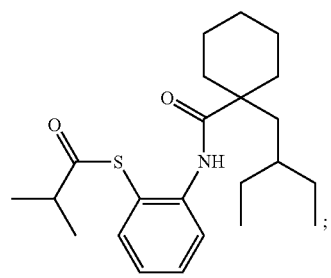
(V)

wherein the composition has less than 0.1% of the compound of formula (X) by weight and less than 0.1% of the compound of formula (V) by weight.

In another embodiment, the present invention provides a composition comprising:
a compound of formula (I):

a compound of formula (X):

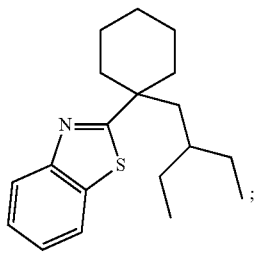

(X)

and a compound of formula (V):

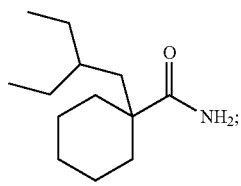

(V)

and having between 1 ppb (parts per billion in weight) and 100 ppm (parts per million in weight) of the compound of formula (X) and between 1 ppb (parts per billion in weight) and 100 ppm (parts per million in weight) of the compound of formula (V), and in particular embodiments having between 1 ppb and 1 ppm of the compound of formula (X) and between 1 ppb and 1 ppm of the compound of formula (V).

In another embodiment, the invention provides a pharmaceutical composition comprising a compound of formula (I), also known as thioisobutyric acid S-(2-{[1-(2-ethyl-butyl)-cyclohexanecarbonyl]-amino}-phenyl)ester, S-[2-([[1-(2-ethylbutyl)-cyclohexyl]-carbonyl]amino)phenyl]2-methyl-propanethioate or dalcetrapib, and a compound of formula (X). In particular, the composition comprises a compound of formula (I) and between 1 ppb and 100 ppm of a compound of formula (X), more particularly between 1 ppb and 1 ppm.

In another embodiment, the invention provides a pharmaceutical composition comprising a compound of formula (I) and a compound of formula (V). In particular, the composition comprises a compound of formula (I) and between 1 ppb and 100 ppm of a compound of formula (V), and more particularly between 1 ppb and 1 ppm.

In another embodiment, the invention provides a pharmaceutical composition comprising a compound of formula (I), a compound of formula (X) and a compound of formula (V). In particular embodiments, the composition comprises a compound of formula (I), between 1 ppb and 100 ppm of a compound of formula (X) and between 1 ppb and 100 ppm of a compound of formula (V).

In general, the nomenclature used herein is based on AUTONOM™ 2000, a Beilstein Institute computerized system for the generation of IUPAC systematic nomenclature. Chemical structures shown herein were prepared using MDL ISIS™ version 2.5 SP2. Any open valency appearing on a carbon, oxygen or nitrogen atom in the structures herein indicates the presence of a hydrogen atom.

The following examples are provided for the purpose of further illustration and are not intended to limit the scope of the claimed invention.

The following abbreviations and definitions are used: Ar (argon); acid chloride (1-(2-ethyl-butyl)-cyclohexanecarbonyl chloride); amidodisulfide (N,N'-(dithiodi-2,1-phenylene) bis[1-(2-ethylbutyl)-cyclohexanecarboxamide]); amidothiophenol (1-(2-ethylbutyl)-N-(2-mercaptophenyl)-cyclohexanecarboxamide); thioester (S-[2-[1-(2-ethylbutyl) cyclohexanecarbonylamino]-phenyl]2-methylthiopropionate); DTDA (2,2'-dithiodianiline); d.i. (deionized); eq. (equivalent); EtOH (ethanol); g (gram); HPLC (high-performance liquid chromatography); GC (gas chromatography); h (hour); M (Molarity [moles/L]); MeOH (methanol); ml (milliliter); and RT (room temperature).

The pressure indicated in the experiments is the gauge pressure, i.e. the pressure relative to the local atmospheric pressure.

Example 1

Synthesis of S-[2-[1-(2-ethylbutyl)cyclohexanecarbonylamino]-phenyl]2-methylthiopropionate A solution of 8.2 g of amidodisulfide (12.9 mmol) in 16.9 g toluene and 6.1 g (38.7 mmol) isobutyric anhydride was transferred together with 552 mg Pd/C (519 μmol Pd, EVONIK E101 N/D 10%) to a 185 mL stainless steel autoclave, which was sealed and 3 times pressurized with 5 bar $H_2$ and released to atmospheric pressure. The autoclave was heated under program control to 80° C., and thereafter charged with 5 bar of $H_2$. The hydrogenation was carried out under vigorous stirring for 18 hrs at the temperature of 80° C. and 5 bar (0.5 MPa). After this time the autoclave was cooled to RT, the pressure released and the reaction mixture filtered. The filtrate was evaporated under 50° C./15 mbar and dissolved in 78 g EtOH. Addition of 22 g d.i. $H_2O$ under Ar at RT leads to the precipitation of 9.67 g thioester (yield 96.3%) as white crystals with a melting point of 64.2-64.4° C. The observed amount of 1-(2-ethylbutyl)-N-(2-mercaptophenyl)-cyclohexanecarboxamide was less than 0.5%.

Example 2

Synthesis of S-[2-[1-(2-ethylbutyl)cyclohexanecarbonylamino]-phenyl]2-methylthiopropionate This example was run in an analogous manner to example 1 but using 12.8 g toluene. After work-up and crystallization, 9.63 g of thioester as white crystals (yield 96%) with 100% HPLC area % purity was isolated.

Example 3

Synthesis of S-[2-[1-(2-ethylbutyl)cyclohexanecarbonylamino]-phenyl]2-methylthiopropionate This example was run in an analogous manner to example 1 but using 26.7 g toluene. After work-up and crystallization, 9.73 g of thioester as white crystals (yield 97%) with 100% HPLC area % purity was isolated.

Example 4

Synthesis of S-[2-[1-(2-ethylbutyl)cyclohexanecarbonylamino]-phenyl]2-methylthiopropionate 8.2 g of amidodisulfide (12.9 mmol) in 16.8 g toluene and 6.1 g (38.7 mmol) isobutyric anhydride was transferred together with 552 mg Pd/C (519 μmol Pd, EVONIK E101 N/D 10%) to a 185 mL stainless steel autoclave. It was hydrogenated under vigorous stirring for 3 hrs at the temperature of 90° C. and 5 bar (0.5 MPa). Work-up according to example 1 afforded 9.63 g of thioester as white crystals (yield 95.9%). HPLC analysis showed a purity of 100 area %.

Example 5

Synthesis of S-[2-[1-(2-ethylbutyl)cyclohexanecarbonylamino]-phenyl]2-methylthiopropionate This example was run in an analogous manner to example 1 but using 552 mg 20% Pd(OH)$_2$/C catalyst (519 µmol Pd, wet, ca. 50 weight % H$_2$O), which was washed 3 times first with THF and then 3 times with Toluene before being transferred in the autoclave. The mixture was hydrogenated under vigorous stirring for 5 hrs at the temperature of 80° C. and 5 bar (0.5 MPa). After work-up according to example 1, 9.76 g of thioester as white crystals (yield 97.2%) were recovered. HPLC analysis showed a purity of 100 area %.

Example 6

Synthesis of S-[2-[1-(2-ethylbutyl)cyclohexanecarbonylamino]-phenyl]2-methylthiopropionate This example was run in an analogous manner to example 1 but using 1.15 g 4.78% nPdnAl2O3/Al2O3 catalyst (519 µmol Pd, SDC materials). The mixture was hydrogenated under vigorous stirring for 5 hrs at the temperature of 80° C. and 5 bar (0.5 MPa). Work-up according to example 1 afforded 9.86 g of thioester as white crystals (yield 98.2%). HPLC analysis showed a purity of 100 area %.

Example 7

Synthesis of S-[2-[1-(2-ethylbutyl)cyclohexanecarbonylamino]-phenyl]2-methylthiopropionate 8.2 g of amidodisulfide (12.9 mmol) in 16.8 g toluene and 6.1 g (38.7 mmol) isobutyric anhydride was transferred together with 552 mg Pd/C (519 µmol Pd, EVONIK E101 N/D 10%) to a 185 mL stainless steel autoclave. It was hydrogenated under vigorous stirring for 18 hrs at the temperature of 80° C. and 0.2 bar (0.02 MPa). Work-up according to example 1 afforded 9.39 g of thioester as white crystals (yield 93.5%). HPLC analysis showed a purity of 100 area %.

Example 8

Synthesis of S-[2-[1-(2-ethylbutyl)cyclohexanecarbonylamino]-phenyl]2-methylthiopropionate 8.2 g of amidodisulfide (12.9 mmol) in 16.8 g ethyl acetate and 6.1 g (38.7 mmol) isobutyric anhydride was transferred together with 552 mg Pd/C (519 µmol Pd, EVONIK E101 N/D 10%) to a 185 mL stainless steel autoclave. The mixture was hydrogenated under vigorous stirring for 18 hrs at the temperature of 80° C. and 5 bar (0.5 MPa). HPLC analysis showed complete conversion. Work-up according to example 1 afforded 8.54 g of thioester as white crystals (yield 85.1%). HPLC analysis showed a purity of 100 area %.

Example 9

Synthesis of S-[2-[1-(2-ethylbutyl)cyclohexanecarbonylamino]-phenyl]2-methylthiopropionate This example was run in an analogous manner to example 8 but using tert-butyl methyl ether. It was hydrogenated under vigorous stirring for 18 hrs at the temperature of 80° C. and 5 bar (0.5 MPa). HPLC analysis showed complete conversion. Work-up according to example 1 afforded 8.89 g of thioester as white crystals (yield 88.5%). HPLC analysis showed a purity of 100 area %.

Example 10

Synthesis of S-[2-[1-(2-ethylbutyl)cyclohexanecarbonylamino]-phenyl]2-methylthiopropionate 8.2 g of amidodisulfide (12.9 mmol) in 16.8 g toluene and 4.2 g (38.7 mmol) isobutyryl chloride was transferred together with 552 mg Pd/C (519 µmol Pd, EVONIK E101 N/D 10%) to a 185 mL stainless steel autoclave. The mixture was hydrogenated under vigorous stirring for 18 hrs at the temperature of 80° C. and 5 bar (0.5 MPa). Thereafter the reaction mixture was analyzed with HPLC, showed 70.6% conversion of amidodisulfide and 52% thioester HPLC area %. In addition 2.9 area % of 1-(2-ethylbutyl)-N-(2-mercaptophenyl)-cyclohexanecarboxamide and 14.5 area % of 2-[1-(2-ethyl-butyl)-cyclohexyl]-benzothiazole were formed.

Example 11

Synthesis of S-[2-[1-(2-ethylbutyl)cyclohexanecarbonylamino]-phenyl]2-methylthiopropionate This example was run in an analogous manner to example 10 but using 2.0 eq. isobutyric anhydride (4.1 g, 25.8 mmol) as reagent. The mixture was hydrogenated under vigorous stirring for 18 hrs at the temperature of 80° C. and 5 bar (0.5 MPa). HPLC analysis showed complete conversion. Work-up according to example 1 afforded 7.05 g of thioester as white crystals (yield 68.5%). HPLC analysis showed a purity of 100 area %.

Example 12

Synthesis of S-[2-[1-(2-ethylbutyl)cyclohexanecarbonylamino]-phenyl]2-methylthiopropionate 8.2 g of amidodisulfide (12.9 mmol) in 22.9 g isobutyric anhydride (145 mmol) was transferred together with 552 mg Pd/C (519 µmol Pd, EVONIK E101 N/D 10%) to a 185 mL stainless steel autoclave. The mixture was hydrogenated under vigorous stirring for 18 hrs at the temperature of 80° C. and 5 bar (0.5 MPa). HPLC analysis showed complete conversion. Work-up according to example 1 afforded 9.57 g of thioester as white crystals (yield 95.3%). HPLC analysis showed a purity of 100 area %.

Example 13

1-(2-ethylbutyl)-N-(2-mercaptophenyl)-cyclohexanecarboxamide 8.2 g of amidodisulfide (12.9 mmol) in 22.9 g toluene was transferred together with 552 mg Pd/C (519 µmol Pd, EVONIK E101 N/D 10%) to a 185 mL stainless steel autoclave. It was hydrogenated under vigorous stirring for 18 hrs at the temperature of 80° C. and 10 bar (1.0 MPa). Thereafter the reaction mixture was analyzed with HPLC, showed 100% conversion of amidodisulfide and 99.2% amidothiophenol HPLC area %.

Example 14

Synthesis of S-[2-[1-(2-ethylbutyl)cyclohexanecarbonylamino]-phenyl]2-methylthiopropionate 8.2 g of amidodisulfide (12.9 mmol) in 16.8 g toluene and 6.1 g (38.7 mmol) isobutyric anhydride was transferred together with 327 mg Raney-Ni (2.59 mmol Ni, EVONIK B113 Z 46.5%) to a 185 mL stainless steel autoclave. It was hydrogenated under vigorous stirring for 18 hrs at the temperature of 100° C. and 1 bar (0.1 MPa). Thereafter the reaction mixture was analyzed with HPLC, showing 100% conversion of amidodisulfide and 100% thioester.

Example 15

Synthesis of S-[2-[1-(2-ethylbutyl)cyclohexanecarbonylamino]-phenyl]2-methylthiopropionate 8.2 g of amidodisulfide (12.9 mmol) in 16.8 g toluene and 6.1 g (38.7 mmol) isobutyric anhydride was transferred together with 1.35 g Nanoparticulate Palladium(0) microencapsulated in polyurea matrix (NP Pd(0) Encat™ 30, sold by Sigma-Aldrich®)(540 μmol Pd, 0.4 mmol Pd/g) to a 185 mL stainless steel autoclave. It was hydrogenated under vigorous stirring for 18 hrs at the temperature of 90° C. and 30 bar (3 MPa). Thereafter the reaction mixture was analyzed with HPLC, showed complete conversion of amidodisulfide and 100% desired product. This catalyst was reused under the same condition for further 10 times, all of them showed the same result i.e. complete conversion and 100% desired product.

Example 16

Synthesis of S-[2-[1-(2-ethylbutyl)cyclohexanecarbonylamino]-phenyl]2-methylthiopropionate In the table hereunder, the reactions were carried in analogous manner to example 1, wherein the reaction conditions were: 0.314 mmol amidodisulfide in 410 mg toluene, 3 eq. isobutyric anhydride, 0.0403 eq. metal catalyst (specifically mentioned in the following table), 80° C., 5 bar, reaction time 18 hrs. Thereafter the reaction mixture was analyzed with HPLC.

| Catalysts | Conversion HPLC [area %] | Yield HPLC [area %] |
|---|---|---|
| 3% Au/TiO2 | 69 | 65 |
| 5% Ru/Al$_2$O$_3$ | 81.1 | 71.8 |
| 5% Pt/C | 99.0 | 73.0 |
| 5% Rh/C | 87.0 | 73.0 |
| 93% Co_Al (~50% H2O) | 49.0 | 43.0 |
| 5% Ir/CaCO3 | 70.0 | 65.5 |

Unless stated to the contrary, all compounds in the examples were prepared and characterized as described. All ranges recited herein encompass all combinations and sub-combinations included within that range limit. All patents and publications cited herein are hereby incorporated by reference in their entirety.

The invention claimed is:

1. A compound of formula (X):

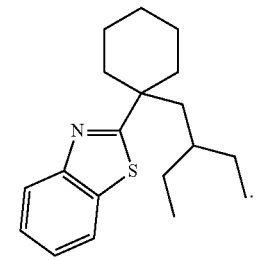

(X)

2. A pharmaceutical composition comprising a compound of formula (I):

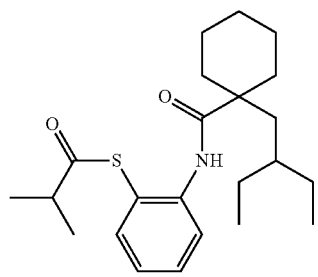

(I)

and a compound of formula (X):

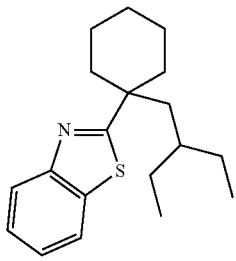

(X)

wherein said composition has less than 0.1% of the compound of formula (X) by weight.

3. A pharmaceutical composition according to claim 2 wherein said composition has between 1 ppb and 100 ppm of the compound of formula (X).

4. A pharmaceutical composition comprising a compound of formula (I):

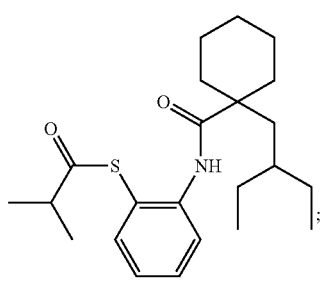

(I)

a compound of formula (X):

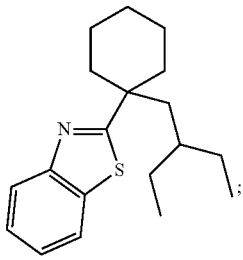

and a compound of formula (V):

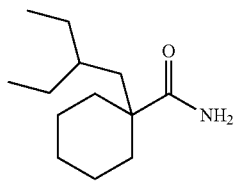

having less than 0.1% of the compound of formula (X) by weight and less than 0.1% of the compound of formula (V) by weight.

5. The pharmaceutical composition of claim 4, having between 1 ppb and 100 ppm of the compound of formula (X) and between 1 ppb and 100 ppm of the compound of formula (V).

6. A pharmaceutical composition comprising S-[2-([[1-(2-ethylbutyl)-cyclohexyl]-carbonyl]amino)phenyl]-methyl-propanethioate and a compound of formula (X)

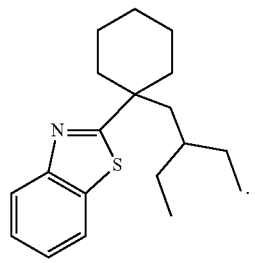

7. The pharmaceutical composition according to claim 6, wherein the composition comprises between 1 ppb and 100 ppm of the compound of formula (X).

* * * * *